United States Patent

Kleiner et al.

[11] 4,173,601
[45] Nov. 6, 1979

[54] CARBAMOYL-OXYALKYL-PHOSPHINIC ACID DERIVATIVES

[75] Inventors: Hans-Jerg Kleiner, Kronberg; Fritz Linke; Walter Dürsch, both of Königstein, all of Fed. Rep. of Germany

[73] Assignee: Hoechst Aktiengesellschaft, Frankfurt am Main, Fed. Rep. of Germany

[21] Appl. No.: 913,548

[22] Filed: Jun. 8, 1978

[30] Foreign Application Priority Data

Jun. 10, 1977 [CH] Switzerland ............ 7192/77

[51] Int. Cl.² ............ C07F 9/32; C09K 3/28
[52] U.S. Cl. ............ 260/938; 106/15.05; 260/970
[58] Field of Search ............ 260/938, 928, 970

[56] References Cited

U.S. PATENT DOCUMENTS 2,957,931  10/1960  Hamilton et al. ............ 260/970 X

FOREIGN PATENT DOCUMENTS 2024280  12/1971  Fed. Rep. of Germany ............ 260/938

Primary Examiner—Anton H. Sutto
Attorney, Agent, or Firm—Connolly and Hutz

[57] ABSTRACT

Carbamoyl-oxyalkyl-phosphinic acid derivatives or mixtures thereof of the formula

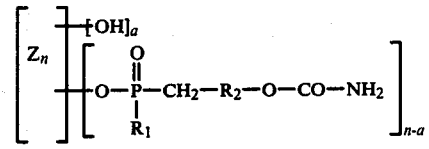

in which $Z_n$ is an n-valent, saturated $C_1$–$C_6$-hydrocarbon group, $R_1$ is an optionally branched $C_1$–$C_6$-alkyl group, which group may be substituted by a halogen atom, or a phenyl group, $R_2$ is an optionally branched $C_2$–$C_7$-alkylene group, a is zero to n-1 and n is an integer of from 1 to 4. These compounds can be prepared by reacting phosphonites of the formula II

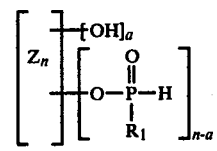

in the presence of radical-forming agents, with a carbamate of the formula III $$CH_2=R_3-O-CO-NH_2 \quad \text{III}$$

in which $R_3$ is an optionally branched $C_2$–$C_7$-alkylene group and is identical with the radical $R_2$ containing one hydrogen atom less. The compounds are used as flame-retardants for textiles.

2 Claims, No Drawings

CARBAMOYL-OXYALKYL-PHOSPHINIC ACID DERIVATIVES

It is the object of the present invention to provide carbamoyl-oxyalkyl-phosphinic acid derivatives or mixtures thereof of the formula

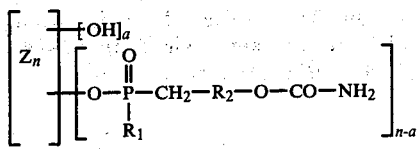

in which $Z_n$ is an n-valent, saturated hydrocarbon radical having from 1 to 6 carbon atoms, $R_1$ is an optionally branched alkyl group having from 1 to 6 carbon atoms, which alkyl group may be substituted by a halogen atom, preferably chlorine, or a phenyl radical, $R_2$ is an optionally branched alkylene group having from 2 to 7 carbon atoms, a is zero to n-1 and n is in the range of from 1 to 4.

The compounds of the invention can be prepared in a good yield by reacting phosphonites of the formula II

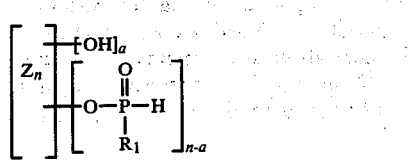

in which Z, $R_1$, n and a have the above meanings, in the presence of radical-forming agents, with olefinically unsaturated carbamates of the formula III

in which $R_3$ is an optionally branched alkylene radical having from 2 to 7 carbon atoms and is identical with the radical $R_2$ containing one hydrogen atom less.

In the case of a being zero and n=1 the phosphonites of formula II are known compounds. Suitable compounds are, for example, methane-phosphonous acid monomethyl ester, methanephosphonous acid monoethyl ester, methanephosphonous acid monoisopropyl ester, methane-phosphonous acid monoisobutyl ester, ethane-phosphonous acid monobutyl ester, chloromethyl-phosphonous acid isobutyl ester, phenyl-phosphonous acid isobutyl ester.

The phosphonites of this type may also be transesterified with polyhydric alcohols such as, for example, glycol, butanediol-1,4, hexane-diol-1,6, neopentyl glycol, glycerol, trimethylolpropane and pentaerythritol.

The transesterification can be carried out, for example, by the method G. Borisov (G. Borisov et al., European Polymer Journal 1973, 1077; C.A. 78, 43615 g (1973)). In this process the phosphonites are reacted with the polyhydric alcohols in an amount of 1 mol of the phosphonite for 1 mol of alcoholic group (a=0). It is likewise possible to use the alcoholic groups in an excess, whereby further valuable starting compounds of formula II (a>0) are obtained.

The carbamates of formula III are known. Suitable compounds are, for example, allyl carbamate, methallyl carbamate, 2-methylbuten-(1)-yl carbamate, buten-(1)-yl carbamate, n-hexen-(1)-yl carbamate, allyl carbamate being preferred.

Suitable radical-forming compounds are all compounds of this type, preferably the usual organic peroxides. More individually there are mentioned di-tert.butyl peroxide, tert.butyl-peroxybenzoate, 2,5-dimethyl-bis-2,5-(peroxybenzoate), tert.butylhydroperoxide, dicumyl peroxide, benzoyl peroxide, preferably di-tert-.butyl peroxide. The radical-forming agent is expediently used in an amount of from 0.5 to 5% by weight, preferably 1 to 2% by weight, calculated on the amount by weight of the carbamate used.

It may be advantageous to work in the presence of inert solvents, for example alcohols such as butanol or hexanol, ethers, aromatic hydrocarbons, for example xylene. In general, the reaction is carried out without solvent.

The process of the invention is preferably carried out in the atmosphere of an inert gas, for example argon or nitrogen.

The reaction is carried out at a temperatur in the range of from 100° to 220° C., preferably 130° to 180° C.

To carry out the reaction it proved advantageous to heat the phosphonites of formula II to the desired reaction temperature and then to add in dosed quantities the carbamates of formula III in admixture with the radical-forming agent. The reaction is terminated after 2 to 6 hours, it is approximately quantitative. Alternatively, the starting compounds can be reacted according to other, generally known methods, although the above mode of operation is preferred. The process can also be carried out in continuous manner.

When the reaction is terminated (discontinuous process), the solvent is distillied off under reduced pressure. If the reaction is carried out in the absence of a solvent, readily volatile constituents can be removed by distillation under reduced pressure. The products of the invention obtained as distillation residue have a sufficient purity for industrial use. In many cases they can be used directly without special purification processes.

The compounds for formula I can be used successfully as agents to bring about flame-retardance or for the manufacture of flame-retardant agents.

With formaldehyde the compounds of the invention can be transformed into the corresponding N-methylol compounds which, by processes known for methylol compounds, can be applied to textile material and cross-linked thereon or reacted directly with the fiber, for example in the case of cotton.

The following examples illustrate the invention.

EXAMPLE 1

108 g of methane-phosphonous acid monoethyl ester are heated to 150° C. while stirring under nitrogen. Over a period of 2.5 hours a mixture of 101 g of allyl carbamate and 1 g of di-tert.butyl peroxide are added dropwise and stirring is continued for 1 hour at the above temperature. The mixture is then cooled and distillation is started at 0.2 torr up to an internal temperature of 140° C. 9 g of distillate are obtained. As residue about 205 g of 3-carbamoyl-oxypropylmethylphosphonic acid ethyl ester, $n_D^{21}$:1.4765 are obtained, corresponding to a yield of about 95% of the theory.

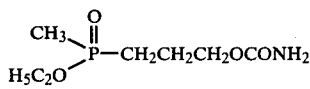

EXAMPLE 2

136 g of methane-phosphonous acid mono-n-butyl ester are heated to 150° C. while stirring in an inert gas. During a period of 2 hours a mixture of 101 g of allyl carbamate and 1 g of di-tert-butyl peroxide is then added dropwise and stirring is continued for 1 hour at the above temperature. Up to an internal temperature of 120° C. and at 0.5 torr efforts are made to bring about distillation but no distillate is obtained. 237 g of 3-carbamoyl-oxypropylmethyl-phosphinic acid n-butyl ester are obtained melting at 56°–57° C. The product can be distilled at 0.6 torr and at 220° C. in a thin layer evaporator.

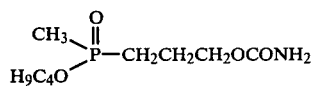

EXAMPLE 3

In a nitrogen atmosphere 100 g of methane-phosphonous acid mono-n-butyl ester are heated to 140° C. while stirring. Over a period of 2 hours a mixture of 85 g of methallyl carbamate and 3.7 g of tert.butyl perbenzoate is added dropwise and stirring is continued for 1 hour at 135° C. Distillation is then started up to an internal temperature of 140° C. and at 0.8 torr, whereby about 5 g of distillate are obtained. 180 g of (3-carbamoyloxy-2-methyl-propyl)methyl-phosphinic acid n-butyl ester are obtained, $N_D^{23}$: 1.4725, corresponding to a yield of about 95% of the theory.

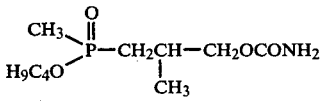

EXAMPLE 4

70 g of methane-phosphonous acid monoisobutyl ester are heated to 150° C. while stirring in an inert gas. Over a period of 2 hours a mixture of 66.5 g of 2-methylbuten-(1)-yl-carbamate and 1.2 g of di-tert.butyl peroxide is added dropwise and stirring is continued for 1 hour at 150° C. The mixture is cooled and distillation is started at 0.5 torr up to an internal temperature of 150° C., whereby 1 g of distillate are obtained. 136 g of (4-carbamoyl-oxy-2-methylbutyl)-methyl-phosphinic acid isobutyl ester, $n_D^{23}$:1.4720, are obtained, corresponding to a yield of over 95% of the theory.

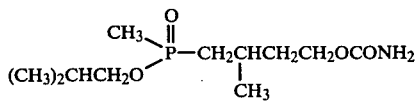

EXAMPLE 5

(a) Transesterification product of methane-phosphonous acid monoisobutyl ester with hexane-diol-1,6 in a molar ratio of 2:1.

In a water jet vacuum of 100 to 20 torrs 408 g of methane phosphonous acid monoisobutyl ester, 177 g of hexane-diol-1,6 and 6 g of soda are heated for 3 hours to 100 to 120° C., whereby 220 g of isobutanol distill off through a column. The residue is filtered with suction. 360 g of a colorless liquid are obtained, $n_D^{20}$:1.4649. The yield exceeds 95% of the theory.

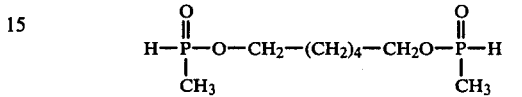

(b) addition product of allyl carbamate on the product according to Example 5 a 360 g of the transesterification product of Example 5 a are heated to 150° C. while stirring in a nitrogen atmosphere. Over a period of 3.5 hours a mixture of 283 g of allyl carbamate and 5 g of di-tert.butyl peroxide is then added dropwise and stirring is continued for 1 hour at 150° C. The mixture is then cooled and distillation is started at 1 torr and up to an internal temperatur of 140° C., whereby about 5 g of distillate are obtained. About 630 g of 3-carbamoyl-oxypropylmethyl-phosphinic acid ester, $n_D^{21}$:1.4930 are obtained, corresponding to a yield of over 95% of the theory.

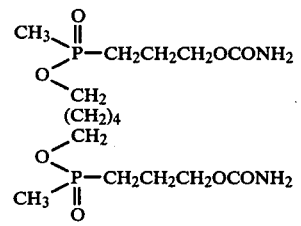

EXAMPLE 6

(a) Transesterification product of methane-phosphonous acid monoisobutyl ester with pentaerythritol in a molar ratio of 4:1.

In a water jet vacuum of 80 to 30 torrs 272 g of methane-phosphonous acid monoisobutylester, 68 g of pentaerythritol and 3 g of soda are heated for 5 hours to 80° to 130° C., whereby 146 g of isobutanol distill off over a column. The residue is filtered with suction. 190 g of a colorless oil, $n_D^{20}$:1.4926 are obtained, corresponding to a yield of about 95% of the theory.

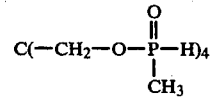

(b) addition product of allyl carbamate on the product of Example 6(a)

184 g of the transesterification product of Example 6(a) are heated to 150° C. while stirring under nitrogen. Over a period of 2 hours a mixture of 188 g of allyl carbamate and 2 g of di-tert.butyl peroxide is added dropwise and stirring is continued for 1 hour at 150° C.

Distillation is then started at 1 torr up to an internal temperature of 150° C., whereby about 5 g of distillate are obtained. About 265 g of 3-carbamoyl-oxypropymethylphosphinic acid ester are obtained which solidifies at about 45° C. This corresponds to a yield of over 95% of the theory.

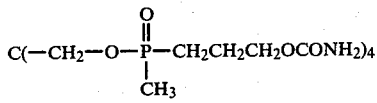

EXAMPLE 7

122 g of methane-phosphonous acid monoisopropyl ester are heated to 150° to 160° C. while stirring under nitrogen. Over a period of 1.25 hours a mixture of 101 g of allyl carbamate and 1.5 g of di-tert.butyl peroxide are added dropwise and stirring is continued for 30 minutes at the above temperature. The mixture is then cooled and distillation is started at 0.3 torr up to an internal temperatur of 140° C., whereby 4.5 g of distillate are obtained. As residue about 215 g of 3-carbamoyl-oxypropylmethyl-phosphinic acid isopropyl ester, $n_D^{20}$: 1.4728, are obtained, corresponding to a yield of over 95% of the theory.

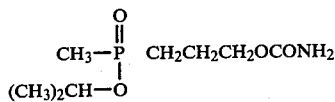

What is claimed is:
1. Compounds of the formula

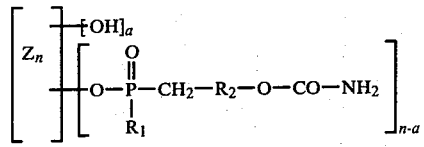

in which
$Z_n$ is an n-valent, saturated hydrocarbon radical having from 1 to 6 carbon atoms,
$R_1$ is an optionally branched alkyl group having from 1 to 6 carbon atoms, which alkyl group may be substituted by a halogen atom, preferably chlorine, or a phenyl radical,
$R_2$ is an optionally branched alkylene group having from 2 to 7 carbon atoms,
a is zero to n−1 and
n is in the range of from 1 to 4; and the mixtures thereof.

2. A compound of the formula I'

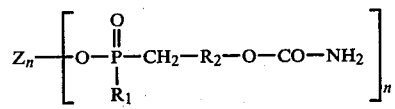

in which
$R_1$ is methyl or ethyl
$R_2$ is ethylene or

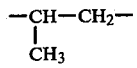

$Z_n$ is an n-valent aliphatic, saturated hydrocarbon radical having from 1 to 6 carbon atoms and
n is in the range of from 1 to 4.

* * * * *